(12) United States Patent
Wehrle et al.

(10) Patent No.: US 10,368,958 B2
(45) Date of Patent: Aug. 6, 2019

(54) SURGICAL CONTAINER CONTENTS DETECTION SYSTEM

(71) Applicant: Aesculap AG, Tuttlingen (DE)

(72) Inventors: Christian Wehrle, Volkertshausen (DE); Martin Nonnenmann, Wurmlingen (DE)

(73) Assignee: Aesculap AG (DE)

( * ) Notice: Subject to any disclaimer, the term of this patent is extended or adjusted under 35 U.S.C. 154(b) by 0 days.

(21) Appl. No.: 15/575,613

(22) PCT Filed: May 23, 2016

(86) PCT No.: PCT/EP2016/061589
§ 371 (c)(1),
(2) Date: Nov. 20, 2017

(87) PCT Pub. No.: WO2016/188959
PCT Pub. Date: Dec. 1, 2016

(65) Prior Publication Data
US 2018/0153639 A1   Jun. 7, 2018

(30) Foreign Application Priority Data

May 26, 2015  (DE) .......................... 10 2015 108 264

(51) Int. Cl.
*A61B 90/98* (2016.01)
*G06K 7/10* (2006.01)
(Continued)

(52) U.S. Cl.
CPC .............. *A61B 90/98* (2016.02); *A61B 50/20* (2016.02); *A61B 50/30* (2016.02); *A61B 50/33* (2016.02);
(Continued)

(58) Field of Classification Search
CPC ................................ A61B 90/98; A61B 50/30
(Continued)

(56) References Cited

U.S. PATENT DOCUMENTS

| 5,996,889 A | 12/1999 | Fuchs et al. |
| 6,426,041 B1 * | 7/2002 | Smith ...................... A61L 2/26 |
| | | 206/223 |

(Continued)

FOREIGN PATENT DOCUMENTS

| DE | 19614719 A1 | 10/1997 |
| DE | 10014542 A1 | 10/2001 |

(Continued)

OTHER PUBLICATIONS

German Search Report for German Application No. 10 2015 108 264.0, with translation, dated Feb. 12, 2016—16 Pages.

(Continued)

*Primary Examiner* — Qutbuddin Ghulamali
(74) *Attorney, Agent, or Firm* — RatnerPrestia

(57) ABSTRACT

A surgical or medical container content detection system includes a container content sensor device for arrangement in a sterilization container. The container content sensor device includes a carrier and at least one sensor arranged or formed on the carrier for detecting at least one identification element which is arranged or formed on an object stored in the sterilization container for the identification thereof. A carrier module arranged on the carrier includes a detection device for detecting at least one detected identification element and is arranged for the purpose of wirelessly transmitting information about the object identified by the detected identification element to the outside of the sterilization container.

16 Claims, 1 Drawing Sheet

(51) Int. Cl.

| | | |
|---|---|---|
| *A61B 50/20* | (2016.01) | |
| *A61B 50/30* | (2016.01) | |
| *A61B 50/33* | (2016.01) | |
| *G06K 19/07* | (2006.01) | |
| *H04B 17/27* | (2015.01) | |
| *G16H 40/63* | (2018.01) | |
| *A61B 17/00* | (2006.01) | |
| *A61B 50/00* | (2016.01) | |
| *A61B 90/90* | (2016.01) | |
| *A61B 90/00* | (2016.01) | |
| *G16H 40/20* | (2018.01) | |
| *H04B 5/00* | (2006.01) | |

(52) U.S. Cl.
CPC ..... *G06K 7/10188* (2013.01); *G06K 7/10366* (2013.01); *G06K 19/0717* (2013.01); *G06K 19/0723* (2013.01); *G16H 40/63* (2018.01); *H04B 17/27* (2015.01); *A61B 90/90* (2016.02); *A61B 2017/00221* (2013.01); *A61B 2050/005* (2016.02); *A61B 2050/3008* (2016.02); *A61B 2050/3011* (2016.02); *A61B 2090/0813* (2016.02); *G16H 40/20* (2018.01); *H04B 5/0062* (2013.01)

(58) Field of Classification Search
USPC .................................................... 340/539.12
See application file for complete search history.

(56) References Cited

U.S. PATENT DOCUMENTS

| | | | |
|---|---|---|---|
| 7,701,334 B1* | 4/2010 | Perkins | G06Q 10/06 340/539.13 |
| 2006/0043179 A1* | 3/2006 | Nycz | A61B 50/33 235/385 |
| 2006/0145871 A1 | 7/2006 | Donati et al. | |
| 2006/0244593 A1* | 11/2006 | Nycz | A61F 2/4425 340/572.1 |
| 2007/0160494 A1* | 7/2007 | Sands | A61L 2/07 422/26 |
| 2008/0142605 A1* | 6/2008 | Butsch | B01L 9/00 235/492 |
| 2008/0150722 A1* | 6/2008 | Jackson | A61L 2/186 340/572.4 |
| 2010/0252626 A1 | 10/2010 | Elizondo et al. | |
| 2014/0125482 A1 | 5/2014 | Rigsby et al. | |

FOREIGN PATENT DOCUMENTS

| | | |
|---|---|---|
| DE | 102006060176 A1 | 6/2008 |
| DE | 102007056261 A1 | 11/2008 |
| DE | 102011050333 A1 | 11/2012 |
| WO | 2009003231 A1 | 1/2009 |

OTHER PUBLICATIONS

International Search Report and Written Opinion for International Application No. PCT/EP2016/061589, dated Jul. 8, 2016—11 Pages.

* cited by examiner

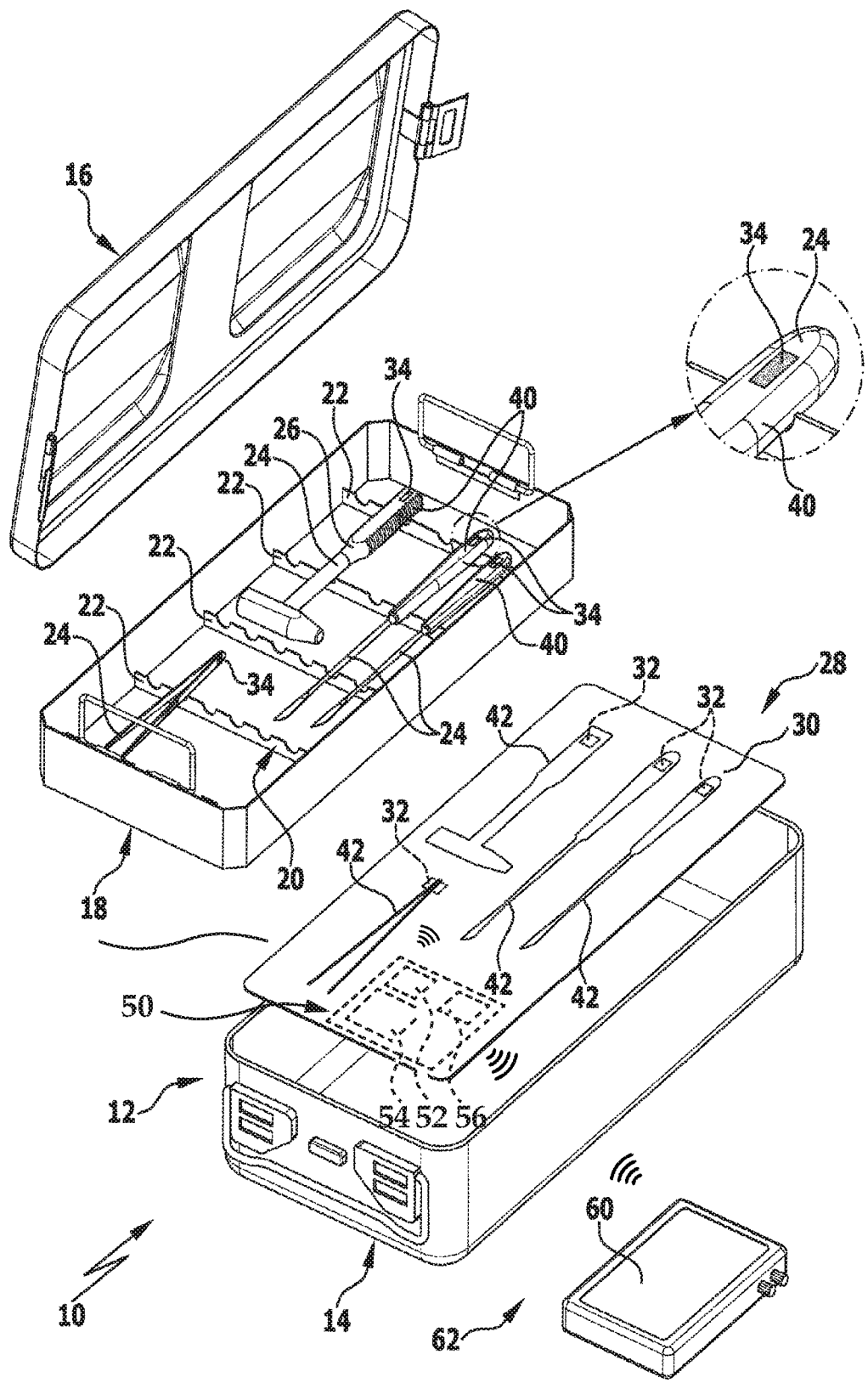

SURGICAL CONTAINER CONTENTS DETECTION SYSTEM

RELATED APPLICATIONS

This application is the United States national phase entry of International Application No. PCT/EP2016/061589, filed May 23, 2016, which is related to and claims the benefit of priority of German Application No. DE 10 2015 108 264.0, filed May 26, 2015. The contents of International Application No. PCT/EP2016/061589 and German Application No. DE 10 2015 108 264.0 are incorporated by reference herein in their entireties.

FIELD

The present disclosure relates to a surgical or medical container content detection system.

BACKGROUND

Detection systems and detection methods for surgical or medical instruments and materials are known from DE 100 14 542 A1, for example. They can be used especially for monitoring and controlling material flow in a hospital. A method and an apparatus for monitoring and controlling the material flow in a hospital are known from DE 196 14 719 A1.

From DE 10 2011 050 333 A1 furthermore a container content detection system comprising a container content sensor device for arrangement in or on a sterilization container is known. The container content sensor device comprises a carrier and at least one sensor arranged or configured on the carrier for detecting an identifying element which is arranged or formed on an object stored in the sterilization container for identifying the same. The container content then is detected by a specific external reader.

It is a drawback in this known arrangement, however, that the external reader is not available at any location and therefore merely a snap-shot at the time of a respective latest detection can be provided. Constantly current data about e.g. a recent sterilization process, a current content and the like are not available. However, the availability of such information and/or data is important, as it has to be determinable at any time which objects are present in a sterilization container. It has to be avoided that, due to the lack of a reading device, a sterilization container has to be opened for checking, especially when the sterilization container including its content has undergone a sterilization process, as otherwise the sterilization container would no longer be sterile after opening.

SUMMARY

An object underlying the invention is to provide an apparatus/arrangement/system by which the content of a sterilization container can be easily and safely determined at any time and which permits tracking of sterilization containers in their environment of use.

This object is achieved by a surgical or medical container content detection system/arrangement.

A reader, for example an RFID reader, is mounted in or on a sterilization container system/arrangement so that said reader can detect the instruments deposited there and removed therefrom. The reader is connected to an energy supply unit as well as a wirelessly operating (wireless) radio module. With the aid of said radio module detected RFID data can be transmitted to a terminal equipment (e.g. a tablet computer, a notebook computer, a smartphone or the like) and can be evaluated there. The reader, the radio module as well as an energy supply unit for supplying the same are cast or combined to form a unit such that said unit can also be sterilized. Preferably, said unit is mat-shaped. The radio module has a transmission power which is dimensioned so that data transmission from the interior of the sterilization container to the outside can take place. Especially the radio module can operate by means of low-energy Bluetooth with low current consumption. Furthermore, the radio module may have a relay function for turning the reader on and/or off. A temperature, humidity and/or pressure level sensor may be provided and adapted to be coupled. The radio module further may have a separate and, resp., inherent memory which may be in the form of an EEPROM and may provide a data memory for e.g. serial numbers, names, sterilization history, maintenance history and the like. Moreover, especially for tracking sterilization containers a low-energy Bluetooth unit (BLE or BT LE; Bluetooth Low Energy) including an antenna array may be provided for positioning the sterilization container within a storage unit, for example. The energy supply preferably can be performed via a battery, an accumulator, a supercapacitor which may be rechargeable via a plug-in cable connection, by induction and/or by means of thermal generation. Further, a direction identification can be provided which renders e.g. a transport direction of a sterilization container identifiable and usable for tracking and/or positioning purposes.

In detail, the object is achieved by a surgical container content detection system comprising a container content sensor device for arrangement in a sterilization container, said container content sensor device comprising a carrier and at least one sensor arranged or configured on the carrier for detecting at least one identifying element which is arranged or formed on an object stored in the sterilization container for identification thereof. A carrier module arranged on the carrier has a detection device for detecting at least one detected identification element and is arranged for the purpose of wirelessly transmitting information about the object identified by the detected identification element to the outside of the sterilization container. In this way, advantageously a RFID reader is provided in/on a sterile container system for detecting deposited and/or removed instruments including those present in a container, said RFID reader forming a separate unit which can be operated without any functionally mechanical connection to the sterile container system and thus can be used as an option to the sterile container system.

Of preference, the container content sensor device includes at least one data transmission unit and a wireless interface for transmitting and/or extracting detection signals generated by the at least one sensor to a read-out and/or evaluating unit external to the container for determining the objects stored in the sterilization container in response to detection signals generated by the at least one sensor. By reason of the wireless transmission of information across the housing wall, which would not be possible on the basis of RFID due to the shielding effect thereof, there are high degrees of freedom in selecting, configuring and coupling compatible terminal equipment. Manual interventions in a sterilization container, for example during storage or tracking, are not required.

Of preference, the carrier module includes at least one sensor forming a transponder reading unit, an energy supply unit for supplying energy to the container content sensor device and/or a wirelessly operating data transmission unit for transmitting detected data and/or detection signals to a read-out and/or evaluating unit external to the container, and the carrier module is cast to form a unit adapted to be steam-pressure sterilized. Due to the fact that the unit of RFID reader, wireless module and energy supply unit is completely cast, the entire unit can also be sterilized. Moreover, the entire unit can be prefabricated and, as such, be provided for embedding at a predetermined location on the carrier, thus allowing additional degrees of freedom to result for different sizes of carriers.

Of preference, the carrier module includes a temperature, humidity and pressure level detection device. A temperature, humidity and pressure level detection device mounted in the interior of the container facilitates direct and precise recording or logging of data and parameters relevant to the operation, as at least during a current sterilization process the sterile container is usually locked in a sterilizer and is not accessible any more.

Of preference, the carrier module includes a storage unit for storing fixed data and at least intermediately storing detected data, wherein the storage unit is arranged to permanently store at least identification information of the sterilization container comprising at least a serial number or an identification of the same, and/or to intermediately store data generated by a temperature, humidity and pressure level detection device in relation to a temperature curve, humidity curve or pressure level curve on the sterilization container which include at least information about a recent sterilization period or a number of sterilization cycles, data detected by the at least one sensor concerning the identification elements or data concerning a sterilization history and/or a maintenance history of the sterilization container. A storage unit inherent to the container offers advantages in recording operation-relevant data and parameters and permits an unambiguous identification of a sterilization container. When plural sterilization containers are provided in spatial vicinity, by wireless reading of locally stored information an inquiry throughout plural containers, a search for a particular container and the like can be safely and easily carried out.

Of preference, the carrier module includes a relay function configured for activating and/or deactivating at least parts of the container content sensor system including the carrier module itself, wherein the relay function is capable of self-release in response to changes of condition detected on the carrier module or is capable of remote-release dependent or independent of said changes of condition. For a largely contactless usability it is advantageous when electric components internal to the container activate themselves and also deactivate themselves again, i.e. when they can turn at least to a stand-by condition when required and depending on the condition. For example, upon detecting an increase in temperature a data detecting and storing operation can be automatically started, after lapse of a predetermined period of time a transfer to an energy-saving sleep condition can be provided and a wake-up function including subsequently predetermined functionality in the case of wireless addressing of a container by an external terminal equipment and the like can be implemented. In total, malfunctions are reduced and the operating safety of the system is increased.

Of preference, the energy supply unit is arranged for an intrinsic energy supply of the container content sensor device and it comprises at least one rechargeable energy storage unit which can be supplied with electrical energy generated on the container side inductively and/or by means of thermal generation. An intrinsic energy supply advantageously generates the energy required for operating electric devices of the system on its own from changes of condition to which it is subjected. The local storage ensures relay functions, as afore-mentioned, data holding functions and the like. There can be provided a signal unit designed for indicating an energy storage condition decreasing in a predetermined way in the case of quite long non-use, for example a signal lamp or a buzzer on a sterilization container itself, or automatic transmission of an indicating information to a reachable terminal equipment or a central administration unit by means of wireless transmission for informing about a particular monitoring condition.

Of preference, the carrier module is arranged to provide, in combination with a highly accurate indoor positioning and BLE conformity in relation to the energy self-supply of the container content sensor device, a device for sterilization container tracking and/or positioning based on a RSSI value and/or a direction identifying device. Intelligent design and/or software routines which are carried in a central processing unit provided on the carrier module, which may be, for example a SOC component or a processor, can advantageously supply required data and information and at least assist tracking, positioning and direction identification capabilities. In total, in this way investment costs are reduced, as already existing hardware can be used. In addition, as hardware restrictions are omitted, the complexity and error proneness of the RFID system are reduced, service and maintenance for a software-based solution are negligible, more universal and more cost-efficient.

Of preference, the at least one sensor is arranged to detect identification elements in the form of transponders. In a simple manner, for example identification elements in the form of transponders can be detected and evaluated when the detector is in the form of a transponder reading device.

Of preference, the at least one sensor is configured in the form of a transponder and is received in a recess of the carrier. Transponders may be provided to be small, compact and cost-efficient for configuring the system. Preferably, the transponder is in the form of a RFID transponder. Transponders of this type are small and are inexpensively available on the market. Furthermore, the at least one sensor is advantageously disposed in a recess of the carrier and can be protected in this way, for example against superheated steam application in the course of a sterilization process.

Of preference, the carrier surrounds the carrier module and the at least one sensor at least partially by form closure and is made from steam-pressure sterilizable material. An especially proper protection of the at least one sensor can be obtained when the carrier completely surrounds the at least one sensor. Stability of the carrier can be improved, for example, in that the carrier surrounds the at least one sensor at least partially by form closure. Preferably, the carrier surrounds the at least one sensor completely by form closure. Thus, undesired cavities which may moreover be penetrated by humidity in the most adverse case can be avoided. In order to enable re-use of the container content sensor device, it is advantageous when the carrier is made from steam-pressure sterilizable material. Then the container content sensor device can be retained in the sterilization container, for example, before the latter is equipped with non-sterile objects again so as to subsequently undergo a sterilization process.

Of preference, the carrier is made from plastic material. The container content sensor device can be manufactured especially easily and cost-efficiently when the carrier is made from plastic material. The carrier may especially be a rigid or else flexible or elastic carrier.

Of preference, the carrier is in the form of a mat. It is favorable when the carrier is in the form of an insertable mat.

The latter may especially include also protruding nubs so as to protect objects to be stored in the sterilization container from damage. In particular, nubs may be designed to have a shock-absorbing effect. Since, according to the invention, no electric or mechanical connections to the outside of the carrier are required, the mat-shaped carrier is suited as an optional system component, i.e. a sterilization container may be used with or without an inserted carrier, as required. Due to the lack of electric and mechanical connections to the outside of the carrier, it is moreover possible to make use of a carrier of a particular size and, resp., having particular dimensions in a plurality of differently sized sterilization containers.

Of preference, the carrier may be in the form of an insertion pattern on which objects to be stored in the sterilization container are shown at least schematically. For example, on the carrier outlines of the objects may be depicted which show to an operating person or serve as an instruction where and in which way objects have to be stored in the sterilization container. The insertion pattern may also be in the form of a mat, for example. It need not absolutely be rigid or stiff but may as well have a flexible and/or elastic design.

It is also preferred to configure a sterilization container to include a lower container part and an upper container part for closing the lower container part, wherein the container content sensor device can be inserted in the sterilization container free from any mechanical connection. Such configuration also enables, for instance in a safety-critical environment, the content of the sterilization container to be redundantly checked by insertion of plural container content sensor devices so that the failure of one of the container content sensor devices still allows for reliably determining the content of the sterilization container.

Of preference, the system also comprises a screen basket having at least one storing means for at least one object to be stored in the screen basket, the latter being adapted to be introduced to the sterilization container. In other words, the screen basket is preferably designed so that it can be inserted in the lower container part of the sterilization container and the lower container part then can be closed with the screen basket present therein by the upper container part.

Of preference, the container content sensor device is arranged or held in the screen basket. When the screen basket is removed e.g. from the lower container part, thus also the container content sensor device can be removed from the sterilization container.

BRIEF DESCRIPTION OF THE DRAWING FIGURE

Hereinafter the invention shall be described in detail by way of preferred embodiments with reference to the enclosed FIGURE, which illustrates a schematic representation of a container content detection system in accordance with an embodiment of the invention.

DETAILED DESCRIPTION

The FIGURE schematically illustrates a first embodiment of a surgical container content detection system in total denoted with reference numeral 10 or a surgical container content detection system. The container content detection system (system/device) 10 includes a sterilization container 12 preferably having a trough-shaped lower container part 14 and an upper container part 16 forming a cover for closing the lower container part 14. However, the container may as well have a lateral loading door or a similar access.

Moreover, the container content detection system 10, hereinafter also shortly referred to system 10, preferably comprises/has a (separate) screen basket 18 for being inserted in the lower container part 14. Advantageously, in the screen basket 18 a support means 20 is provided which comprises/includes plural strip-shaped supporting elements 22 arranged in parallel to each other and having supporting recesses for storing objects 24 in a defined manner. The objects 24 may especially be medical and surgical instruments exemplified in the FIGURE or implants or implant parts not shown in the FIGURE.

Moreover, the system 10 comprises/has a container content sensor device 28. It comprises/relates to a carrier 30 in the form of e.g. a mat or an insertion pattern. One or more sensors 32 for detecting an identification element 34 are arranged or formed on the carrier 30. At least one such identification element 34 is disposed on each object 24 (to be inserted) so as to be able to unambiguously identify such object. The identification element 34 is preferably configured as a transponder which may be provided in the form of a so-called RFID chip. Preferably, the identification elements 34 are arranged on handle elements 40 of the objects.

With respect to ranges obtainable with RFID, in relation to magnitudes occurring in sterilization containers 12 of the type in question and due to the shielding effect of the container and/or screen basket walls a distinction has to be made primarily between close coupling and remote coupling. In the case of close coupling ranges of 0 to 1 cm are obtainable, i.e. the positions of the sensor 32 and the identification element 34 have to be exactly defined during a reading operation. Due to the close coupling in this case, larger amounts of energy can be made available to the identification element 34 so that applications in which increased safety is relevant can preferably be realized by means of inductive or capacitive close coupling. In the case of remote coupling, obtainable ranges amount to up to 1 m, usually by means of inductive coupling and passive energy supply of the identification element 34 by means of energy transmitted from the magnetic field of a reader.

Accordingly, a single sensor 52 the functioning of which may basically correspond to that of the sensor 32 can be provided in a carrier module 50 still to be described and being arranged at a predetermined position on or in the carrier 30, for example in a rim or corner area thereof, and can centrally detected data and/or information from plural identification elements 34 at respective objects 24 by means of remote coupling, for example. Alternatively, when using a close coupling, plural sensors 32 can be arranged in direct vicinity to each of the identification elements 34 and can be connected, for example via conductive connections (not shown) extending in the carrier 30, to a central processing device (not shown) in the carrier module 50. As a further alternative, a combination, i.e. arrangement of both, aforementioned sensors 32 and 52 can further be realized by means of which for example finely differentiated steps of the container content detection can be achieved (e.g. increased safety by close coupling and respective pairs of sensor identification elements close to e.g. prior-ranking objects vis-à-vis saving options by remote coupling with omission of identification elements at e.g. lower-ranking objects). It would also be imaginable that the screen basket 18 itself, which is made from metal, forms an antenna or that via separate antennas the respective RFID signal is coupled into the metallic basket.

In this embodiment, the carrier module 50 comprises/has a transponder reader or RFID reader which can be formed by the sensor 52, for example, and can be designed for reading out also plural identification elements 34 and/or sensors 32, but may also constitute part of a central detection and processing unit (not shown) with a sensor portion and/or a storage portion, an energy supply device 54 and a wirelessly operating radio module or wireless module 56 by means of which (RFID) data received from the transponder reader can be transmitted to a read-out and/or evaluation unit, for example a terminal equipment in the type of a tablet computer, a notebook computer, a smartphone or the like, outside of the sterilization container 12 for being evaluated there.

The carrier module 50 moreover includes a separate storage unit (not shown), for example EEPROM or flash memory of predetermined size, for storing inside the container data such as e.g. a serial number, a designation or identification, and/or history data relating to sterilization history, maintenance history and the like.

Furthermore, the carrier module 50 preferably includes a temperature, humidity and pressure level sensor (not shown) which may be formed to be integrated in the carrier module 50, for recording a recent sterilization period, a number of completed sterilization cycles and the like. Data detected by the temperature, humidity and pressure level sensor can be stored in the storage unit of the carrier module 50.

In addition, the carrier module 50 preferably has a relay function which is configured for intelligent activation and/or deactivation of the system 10. The intelligent activation and/or deactivation may comprise, for example, a self-controlled change of condition upon detection of a predetermined condition or a predetermined change of condition, or a change of condition remote-triggered via the read-out and/or evaluation unit 62. Realizable intelligence may include, for example, a wake-up function, a standby function and the like in the case of corresponding addressing by the read-out and/or evaluating unit 62, automatic activation upon detection of insertion of a first object 24, for example, or upon closing of the sterilization container 12, automatic deactivation when a predetermined period of time has elapsed without change and the like.

For the rest, the carrier module 50 may be configured for a direction identification. Strongly preferred, a direction identification is carried out independently of hardware by evaluation of the reading data of a reader by means of software so that even without the presence of specific means for direction identification, such as appropriately designed readers or antennas, the direction of an object can be determined. A function for detecting and filtering false-positives may accordingly be provided. In this case, the carrier module 50 is configured for interaction with a direction identification unit preferably operating based on software and is equipped for providing data for direction identification.

Moreover, the carrier module 50 may comprise an energy storage (not shown) for self-supply of the module, the carrier 30 and/or the sterilization container 12 and, resp., the system 10 in total with energy. The energy storage, for example a rechargeable battery or an accumulator and/or a capacitor, preferably a supercapacitor, in this case can be fed via a plug-in energy supply, by means of inductive coupling and/or, especially by exploiting the temperatures and temperature variations occurring during the sterilization process, i.e. the waste heat occurring during the sterilization process, e.g. by means of thermo-generating Peltier elements, for generating electrical energy. In particular thermal generation and Peltier elements are suited for feeding wireless sensors and, in so far, for an at least partial energy self-supply of the system 10 in relevant system conditions.

In combination with a highly accurate indoor positioning, for example of a HAIP type (High Accuracy Indoor Positioning), and BLE (Bluetooth Low Energy) conformity with respect to the energy self-supply of the system 10, i.e. in the case of sufficiently low current absorption especially of the carrier module 50, further with an appropriate antenna arrangement a sterilization container tracking and/or positioning, for example inside a storage, is imaginable based on the BLE RSSI value (Bluetooth Low Energy Received Signal Strength Indicator) or an interior navigation.

In this respect, the carrier module 50 in this embodiment forms a unit which as such is completely cast or enclosed by an appropriate casting material or glass. The casting material as well as all components of the carrier module 50 have such temperature resistance that the entire unit can also be sterilized.

The carrier 30 is preferably made from plastic material and may be rigid and, resp., stiff or else flexible and/or elastic. A flexible and/or elastic configuration is preferably provided when the carrier 30 is in the form of a mat adapted to be inserted in the sterilization container 12. The completely equipped carrier module 50 and the sensors 32, as far as the latter are present, can be glued onto the carrier 30 or alternatively arranged in recesses of the carrier 30 not shown in detail. Preferably, the carrier 30 completely encloses the carrier module 50 and the sensors 32 so as to protect the latter. Preferably, the carrier 30 surrounds the carrier module 50 and the sensors 32 by form closure. For example, the material from which the carrier is made can be surrounded or cast around the carrier module 50 and the sensors 32 for manufacturing the container content sensor device 28.

When the carrier 30 takes the shape of an insertion pattern, preferably contours 42 or pictures of the objects 24 to be stored in the sterilization container 12 are schematically shown. The contours 42 may especially be printed on, engraved in or applied to the carrier 30 by laser labelling or the like.

The sensors 32 are preferably arranged inside the contours 42 or within the area thereof such that they are in closest spatial vicinity to the identification elements 34 when the objects 24 are stored ordered in the screen basket 18.

Possibly present sensors 32, and especially the sensor 52, which are adapted to comprise a coil, for example, are connected to be electrically conducting to the wirelessly operating radio module 56. Electric connecting lines to and from the sensors 32 may be printed onto the carrier 30 or cast into the latter, for example. Due to the wireless data transmission which produces and maintains coupling to the read-out and/or evaluating unit 62 comprised by the system outside of the sterilization container 12, the carrier 30 can be arranged freely in the sterilization container 12, i.e. either at the lower container part 14, at the upper container part 16 or directly in the screen basket 18.

The read-out and/or evaluating unit 62 may especially comprise a display 60 so as to show the content of the sterilization container 12 graphically or in the form of a list. The read-out and/or evaluating unit 62 moreover includes functions of a computer system that allow or at least assist tracking of the objects 24, for example in a hospital.

The afore-described system 10 thus enables coupling of the read-out and/or evaluating unit 62 to preferably each of the provided sensors 32 of the container content sensor device 28. This is useful for transmitting detection signals generated by the sensor(s) 32 to the read-out and/or evaluating unit 62 for establishing the content of the sterilization container 12. The transmission is performed via wireless connection, for example by a radio connection such as Bluetooth so as to transmit detection signals of the sensors 32 to the read-out and/or evaluating unit 62. The carrier module 50 in this case comprises a transmitting and receiving unit suited for contactless transmission of the detection signals.

The described system 10 thus comprises a carrier module 50 forming or comprising a transponder reading device for detecting an identification element 34 and transmitting detected data by means of radio-based data transmission out of the sterilization container 12, and includes, on the one hand, the at least one sensor 52 and/or 32 and, on the other hand, the read-out and/or evaluating unit 62. One or more sensors 32, 52 are arranged as part of the container content sensor device 28 in the interior of the sterilization container 12 so as to generate detection signals in response to the presence of identification elements 34 of objects 24 stored in the sterilization container. The detection signals then are evaluated especially in the read-out and/or evaluating unit 62 coupled to the sensors 32, 52 by a radio-transmission path through the housing wall of the sterilization container, which read-out and/or evaluating unit would be accommodated, in the case of a manual transponder reading device, in a joint housing with the sensors, for example, or would require at least one cable-bound connection.

The arrangement of the container content sensor device 28 in the interior of the sterilization container 12 especially offers the advantage that the container content can be determined even when the sterilization container 12 is closed, especially even when the sterilization container 12 is completely made from metal, for example aluminum. By virtue of the shielding effect of metals to electromagnetic radiation, scanning of the content of the sterilization container 12 by a commercially available manual reader for reading out transponders is not suited. The radio-based coupling to the read-out and/or evaluating unit 62 enables higher degrees of freedom regarding the constructional design thereof and increases the active radius of detection due to the omission of a connecting cable of predetermined length. Furthermore, the error proneness by reason of defective wiring and defective plug-in contacts is reduced and, not least due to the storage of relevant parameters and data in the carrier module 50 and thus independently of the unit 62 directly in the sterilization container 12, compatible read-out and evaluating units 62 can be easily coupled and/or exchanged additionally and/or in parallel or in multiple way, where necessary.

Finally, the insertable carrier 30 including the carrier module 50 and the sensors 32, 52 embedded therein forms an independent separate unit and component of the system 10 which, due to the wireless connection to the external read-out and evaluation requires no further operationally relevant connection to or fixation on the sterilization container 12 and, in this respect, can be optionally used and/or retrofitted.

The invention claimed is:

1. A medical container content detection system, comprising:
   a container content sensor device for arrangement in a sterilization container, which container content sensor device comprises a carrier and at least one sensor arranged or formed on the carrier for detecting at least one identification element which is arranged or formed on at least one object stored in the sterilization container for the identification thereof;
   a carrier module arranged on the carrier, wherein the carrier module includes a detection device for detecting the at least one identification element and an energy supply unit for supplying the container content sensor device with energy, arranged for the purpose of wirelessly transmitting information about the at least one object identified by the at least one identification element by radio-based data transmission to an outside of the sterilization container and is combined to form a steam-pressure sterilizable unit; and
   a screen basket comprising at least one storing means for storing the at least one object, said screen basket being adapted to be introduced to the sterilization container, wherein the container content sensor device is arranged or retained in the screen basket.

2. The medical container content detection system according to claim 1, wherein the container content sensor device includes at least one data transmission device and a wireless interface for transmitting and/or extracting detection signals generated by the at least one sensor to a read-out and/or evaluating unit external to the container for determining the at least one object stored in the sterilization container in response to detection signals generated by the at least one sensor.

3. The medical container content detection system according to claim 1, wherein the at least one sensor forms a transponder reading device and/or a wirelessly operating data transmission device for transmitting detected data and/or detection signals to a read-out and/or evaluating unit external to the container, and the carrier module is cast to form the steam-pressure sterilizable unit and/or is combined by enclosing.

4. The medical container content detection system according to claim 3, wherein the energy supply unit is arranged for energy self-supply of the container content sensor device and comprises at least one rechargeable energy storing unit which can be supplied with electrical energy generated inductively or by means of thermal generation on the container side.

5. The medical container content detection system according to claim 1, wherein the carrier module includes a storage unit for storing fixed data and at least intermediately storing detected data, wherein the storage unit is arranged for permanently storing at least identification information of the sterilization container including at least a serial number or an identification of the same, and/or for intermediately storing at least data generated by a temperature, humidity and/or pressure level detection device in relation to a temperature, humidity and/or pressure level curve at the sterilization container, said data containing at least information about a recent sterilization period or a number of sterilization cycles, data detected by the at least one sensor relating to the identification elements or data relating to a sterilization history and/or a maintenance history of the sterilization container.

6. The medical container content detection system according to claim 1, wherein the carrier module includes a relay function which is configured for activating and/or deactivating at least parts of the container content sensor system including the carrier module itself, wherein the relay function can be self-triggered in response to changes of condition detected on the carrier module or can be remote-triggered dependent on or independent of said changes of conditions.

7. The medical container content detection system according to claim 1, wherein the at least one sensor is arranged for detecting the at least one identification element in the form of a transponder.

8. The medical container content detection system according to claim 1, wherein the at least one sensor is in the form of a transponder and is received in a recess of the carrier.

9. The medical container content detection system according to claim 1, wherein the carrier surrounds the carrier module and the at least one sensor at least partially by form closure and is made from steam-pressure sterilizable material.

10. The surgical container content detection system according to claim 1, wherein the carrier is made from glass or plastic material.

11. The medical container content detection system according to claim 1, wherein the carrier is in the form of a mat.

12. The medical container content detection system according to claim 1, wherein the carrier is in the form of an insertion pattern on which objects to be stored in the sterilization container are shown at least schematically.

13. The medical container content detection system according to claim 1, further comprising a sterilization container comprising a lower container part and an upper container part for closing the lower container part, wherein the container content sensor device can be inserted in the sterilization container free from mechanical connections.

14. The medical container content detection system according to claim 1, wherein the screen basket or a section of the screen basket forms an antenna or can be used as an antenna.

15. A medical container content detection system, comprising:
a container content sensor device for arrangement in a sterilization container, which container content sensor device comprises a carrier and at least one sensor arranged or formed on the carrier for detecting at least one identification element which is arranged or formed on at least one object stored in the sterilization container for the identification thereof; and
a carrier module arranged on the carrier, wherein the carrier module includes a detection device for detecting the at least one identification element and an energy supply unit for supplying the container content sensor device with energy, arranged for the purpose of wirelessly transmitting information about the at least one object identified by the at least one identification element by radio-based data transmission to an outside of the sterilization container and is combined to form a steam-pressure sterilizable unit,
wherein the carrier module is arranged for providing a device for sterilization container tracking and/or positioning based on a Received Signal Strength Indicator value and/or a direction identification device in connection with a high-accuracy indoor positioning and Bluetooth Low Energy conformity in relation to the energy self-supply of the container content sensor device.

16. A medical container content detection system, comprising:
a container content sensor device for arrangement in a sterilization container, which container content sensor device comprises a carrier and at least one sensor arranged or formed on the carrier for detecting at least one identification element which is arranged or formed on at least one object stored in the sterilization container for the identification thereof;
a screen basket including at least one storage unit for the at least one object, which screen basket can be introduced to the sterilization container; and
a carrier module arranged on the carrier which has a detection means for detecting at least one detected identification element and is arranged for the purpose of wirelessly transmitting information about the at least one object identified by the detected identification element to the outside of the sterilization container,
wherein the screen basket or a section of the screen basket forms an antenna or can be used as an antenna.

* * * * *